United States Patent
Kosboth et al.

(10) Patent No.: US 6,755,201 B1
(45) Date of Patent: Jun. 29, 2004

(54) METHOD FOR THE DURABLE SHAPING OF KERATIN FIBERS

(75) Inventors: Celia Kosboth, Duisburg (DE); Anke Eggers, Duesseldorf (DE); Josef Koester, Duesseldorf (DE); Werner Seipel, Hilden (DE); Hermann Hensen, Haan (DE)

(73) Assignee: Cognis Deutschland GmbH & Co. KG, Duesseldorf (DE)

( * ) Notice: Subject to any disclaimer, the term of this patent is extended or adjusted under 35 U.S.C. 154(b) by 219 days.

(21) Appl. No.: 10/018,711

(22) PCT Filed: Jun. 6, 2000

(86) PCT No.: PCT/EP00/05171

§ 371 (c)(1),
(2), (4) Date: Apr. 2, 2002

(87) PCT Pub. No.: WO00/76465

PCT Pub. Date: Dec. 21, 2000

(30) Foreign Application Priority Data

Jun. 15, 1999 (DE) .......................................... 199 27 075

(51) Int. Cl.[7] .............................. A61K 7/06; A61K 7/08
(52) U.S. Cl. ....................... 132/202; 132/203; 132/210; 424/70.2; 424/70.14
(58) Field of Search ................................ 132/202, 203, 132/210; 424/70.2, 70.14

(56) References Cited

U.S. PATENT DOCUMENTS

| | | | |
|---|---|---|---|
| 4,172,887 A | | 10/1979 | Vanlerberghe et al. |
| 5,279,313 A | | 1/1994 | Clausen et al. |
| 5,637,297 A | * | 6/1997 | Savaides et al. .......... 424/70.51 |
| 5,718,891 A | | 2/1998 | Prat et al. |
| 5,753,606 A | | 5/1998 | Hees et al. |
| 5,945,299 A | | 8/1999 | von Kries et al. |

FOREIGN PATENT DOCUMENTS

| | | |
|---|---|---|
| DE | 3914131 | 10/1990 |
| DE | 43 08 794 | 4/1994 |
| DE | 195 02 168 | 6/1996 |
| DE | 195 02 167 | 2/1997 |
| DE | 197 32 015 | 7/1998 |
| FR | 2 252 840 | 12/1978 |
| GB | 2 242 358 | 10/1991 |
| WO | WO 91/01295 | 2/1991 |
| WO | WO 00/76465 | 12/2000 |

OTHER PUBLICATIONS

R.Puchta et al., "A New Generation of Softener", pp. 186–191, vol. 30, Tenside Surf. Det., Carl Hanser Verlag, Munchen, (1993).

M. Brock, "Neue Entwicklungen auf dem Gebiet der Wascheweichspuler", pp. 394–398, vol. 30, Tenside Surf. Det., Carl Hanser Verlag, Munchen, (1993).

R. Lagerman et al., "Synthesis and Performance of Ester Quarternary Biodegradable Softeners", pp 97–100, vol. 71, No. 1, J.Am.Oil.Chem.Soc., (1994).

I.Shapiro et al., "Environmentally Friendly Ester Quats", pp. 77–78,80, vol. 109, Cosmetics & Toiletries, Allured Publishing Corporation, (1994).

G.Schuster et al., "Fette und Öle Tenside Waschmittel", pp. 177–184, vol. 108, Seifen Öle Fette Wachse, (1982).

G.Schuster et. al, "Protein Chemistry as Related to Cosmetics and Toiletries", pp. 63–74, vol. 99, Cosmetics & Toiletries, Allured Publishing Corporation, (1994).

H.W. Steisslinger, "Kollagen–Hydrolysate",pp. 556, 557, 560, 561, 565, 566, vol. 72, Parf.Kosm., Jahrgang,Nr., (1991).

F.Aurich et al., "Enzymatisch hergestellte Proteinhydrolysate", pp. 389–395, vol. 29, Tenside Surf. Det., Carl Hanser Verlag, Muchen, (1992).

J. Falbe, "Surfactants in Consumer Products", pp. 54–124, Springer Verlag, Berlin (1987).

J. Falbe, "Katalysatoren, Tenside und Mineralöladditive", pp. 123–217, Thieme Verlag, Stuttgart, (1978).

Todd et al., "Volatile silicon fluids for cosmetic formulations", pp. 29–32, vol. 91, Cosmetics & Toiletries, (1976).

Dritte, "Kosmetische Farbemittel", pp. 81–106, Farbstoffkomission der Deutschen Forschungsgemeinschaft, Verlag Chemie, Weinheim, (1984).

Wortmann et al., "Characterizing Keratins Using High–Pressure Differential Scanning Calorimetry", pp. 137–150, vol. 48, Journal of Applied Polymer Science, (1993).

* cited by examiner

Primary Examiner—Yogendra N. Gupta
Assistant Examiner—Eisa Elhilo
(74) Attorney, Agent, or Firm—John E. Drach; Steven J. Trzaska

(57) ABSTRACT

A process for deforming keratin fibers involving: (a) mechanically deforming the keratin to form mechanically deformed keratin fibers; and (b) contacting the keratin fibers, prior to and/or after the keratin fibers are mechanically deformed, with an aqueous composition containing: (i) from about 0.1 to 20% by weight of an alkoxylated carboxylic acid ester; and (ii) from about 0.1 to about 20% by weight of a fatty acid partial glyceride, all weights being based on the weight of the composition.

11 Claims, No Drawings

METHOD FOR THE DURABLE SHAPING OF KERATIN FIBERS

BACKGROUND OF THE INVENTION

This invention relates to a process for the permanent deformation of keratin fibers using alkoxylated carboxylic acid esters and partial glycerides and to their use for the production of wave lotions.

The permanent deformation of keratin fibers is normally carried out by mechanically deforming the fibers and fixing the deformation by suitable auxiliaries. Before and/or after their deformation, the fibers are treated with an aqueous preparation of a keratin-reducing substance and, after a contact time, are rinsed with water or with an aqueous solution. In a second step, the fibers are treated with an aqueous preparation of an oxidizing agent. After a certain contact time, the oxidizing agent is also rinsed out and the mechanical deforming aids (curlers, rollers) are removed from the fibers.

The aqueous preparation of the keratin reducing agent is normally alkalized so that the fiber swells and the keratin-reducing substance is thus able to penetrate deeply into the fiber. The keratin-reducing substance splits some of the disulfide bonds of the keratin to -SH groups, so that the peptide linkage is loosened and, through the stretching of the fibers by their mechanical deformation, the keratin structure is re-oriented. Under the influence of the oxidizing agent, disulfide bonds are re-established and, in this way, the deformation which the keratin structure has undergone is fixed.

A known process of the type in question is the permanent waving of human hair. This process may be applied both to produce curls and waves in straight hair and to straighten curly hair.

Although this process known as permanent waving is widely practised today, it still uses preparations which cannot be regarded as optimal in many respects. In particular, it is desirable to reduce the damage—which can go as far as breakage—to mistreated hair, particularly oxidatively pretreated hair, without affecting the required shaping performance and to protect the hair against excessive drying out and moisture loss. The same applies to the frequent problems affecting the scalp through dermatological incompatibility. Another problem is that the preparations thicken easily, particularly when stored at elevated temperature, and cannot then be conveniently used any more.

Accordingly, the problem addressed by the present invention was to provide a process for the permanent deformation of keratin fibers, particularly human hair, which would be free from the disadvantages mentioned above.

DESCRIPTION OF THE INVENTION

The present invention relates to a process for the permanent deformation of keratin fibers in which the fibers are treated before and/or after mechanical deformation with an aqueous preparation of a keratin-reducing substance, rinsed with a first rinse after a contact time, then fixed with an aqueous preparation of an oxidizing agent and rinsed again after a contact time, characterized in that an aqueous preparation of the keratin-reducing substance and/or the oxidizing agent containing (a) 0.1 to 20% by weight of alkoxylated carboxylic acid esters and (b) 0.1 to 20% by weight of fatty acid partial glycerides, with the proviso that the quantities shown add up to 100% by weight with water and optionally other auxiliaries and additives, is used.

It has surprisingly been found that a significant reduction in the damage to the hair can be achieved with the shaping performance intact or even increased providing the water-based preparations used contain a mixture of alkoxylated carboxylic acid esters and fatty acid partial glycerides. These mixtures lead after deformation to stabilization and invigoration of the hair and, hence, also afford the hair protection against drying out and moisture loss. In addition, the preparations are dermatologically very safe. The invention includes the observation that performance can be further improved if esterquats and/or protein hydrolyzates are additionally used.

Alkoxylated Carboxylic Acid Esters

The alkoxylated carboxylic acid esters which the preparations according to the invention must contain as component (a) are known from the prior art. They may be obtained, for example, by esterification of alkoxylated carboxylic acids with alcohols. For the purposes of the present invention, however, the compounds are preferably produced by reaction of carboxylic acid esters with alkylene oxides using catalysts, more especially calcined hydrotalcite in accordance with DE 3914131 A, which give compounds with a narrow homolog distribution. Carboxylic acid esters of both monohydric alcohols and dihydric alcohols can be alkoxylated by this process. Alkoxylated carboxylic acid esters of monohydric alcohols corresponding to general formula (I):

$$R^1CO(OAlk)_nOR^2 \qquad (I)$$

in which $R^1CO$ is an aliphatic acyl group derived from a carboxylic acid, AlkO stands for alkylene oxide and $R^2$ is an aliphatic alkyl group derived from a monohydric aliphatic alcohol, are preferred for the purposes of the invention. Alkoxylated carboxylic acid esters of formula (I), in which $R^1CO$ is an aliphatic acyl group containing 6 to 30, preferably 6 to 22 and more particularly 10 to 18 carbon atoms, AlkO stands for a $CH_2CH_2O$—, $CHCH_3CH_2O$— and/or $CH_2$—$CHCH_3O$ group, n has an average value of 1 to 30, preferably 5 to 20 and more particularly 10 to 15 and $R^2$ is a linear or branched alkyl group containing 1 to 4 and preferably 1 and/or 2 carbon atoms, more particularly methyl, are particularly suitable.

Preferred acyl groups are derived from carboxylic acids containing 6 to 22 carbon atoms of natural or synthetic origin, more especially from linear, saturated and/or unsaturated fatty acids, including the technical mixtures thereof obtainable by lipolysis from animal and/or vegetable fats and oils, for example from coconut oil, palm kernel oil, palm oil, soya oil, sunflower oil, rapeseed oil, cottonseed oil, fish oil, bovine tallow and lard. Examples of such carboxylic acids are caproic acid, caprylic acid, 2-ethyl hexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and/or erucic acid.

AlkO stands for the alkylene oxides which are reacted with the carboxylic acid esters and which comprise ethylene oxide, propylene oxide and/or butylene oxides, preferably ethylene oxide and/or propylene oxide and more particularly ethylene oxide on its own.

Alkoxylated carboxylic acid esters corresponding to formula (I), in which $R^1CO$ is a linear or branched, saturated or unsaturated acyl group containing 10 to 18 carbon atoms, AlkO is a $CH_2CH_2O$ group, n is a number of 5 to 20 and $R^2$ is a methyl group, are particularly suitable. Examples of such compounds are lauric acid methyl ester, coconut fatty acid methyl ester and tallow fatty acid methyl ester alkoxylated with on average 5,7,9 or 11 moles ethylene oxide.

The alkoxylated carboxylic acid esters may be used in quantities of 0.1 to 20, preferably 0.5 to 10 and more preferably 1 to 5% by weight, based on the keratin-reducing substance or the oxidizing agent, in the process according to the invention.

Fatty acid Partial Glycerides

Fatty acid partial glycerides which form component (b), i.e. monoglycerides, diglycerides and technical mixtures thereof, may still contain small quantities of triglycerides from their production. The partial glycerides preferably correspond to formula (II):

in which $R^3CO$ is a linear or branched, saturated and/or unsaturated acyl group containing 6 to 22 and preferably 12 to 18 carbon atoms, $R^4$ and $R^5$ independently of one another have the same meaning as $R^3CO$ or represent OH and the sum (a+b+c) is 0 or a number of 1 to 100 and preferably 5 to 25, with the proviso that at least one of the two substituents $R^4$ and $R^5$ represents OH. Typical examples are mono- and/or diglycerides based on caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and technical mixtures thereof. Oleic acid monoglycerides are preferably used. The fatty acid partial glycerides may be used in quantities of 0.1 to 20, preferably 0.5 to 10 and more preferably 1 to 5% by weight, based on the keratin-reducing substance or the oxidizing agent, in the process according to the invention.

Esterquats

"Esterquats" are generally understood to be quaternized fatty acid triethanolamine ester salts. They are known compounds which may be obtained by the relevant methods of preparative organic chemistry, cf. International patent application WO 91/01295 (Henkel), in which triethanolamine is partly esterified with fatty acids in the presence of hypophosphorous acid, air is passed through the reaction mixture and the whole is then quaternized with dimethyl sulfate or ethylene oxide. In addition, German patent DE 4308794 C1 (Henkel) describes a process for the production of solid esterquats in which the quaternization of triethanolamine esters is carried out in the presence of suitable dispersants, preferably fatty alcohols. Overviews of this subject have been published, for example, by R. Puchta et al. in Tens. Surf. Det., 30, 186 (1993), by M. Brock in Tens. Surf. Det., 30, 394 (1993), by R. Lagerman et al. in J. Am. Oil Chem. Soc., 71, 97 (1994) and by I. Shapiro in Cosm. Toil. 109, 77 (1994).

The quaternized fatty acid triethanolamine ester salts correspond to formula (III):

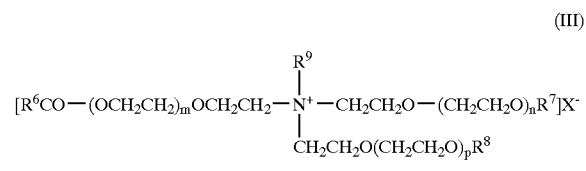

in which $R^6CO$ is an acyl group containing 6 to 22 carbon atoms, $R^7$ and $R^8$ independently of one another represent hydrogen or have the same meaning as $R^6CO$, $R^9$ is an alkyl group containing 1 to 4 carbon atoms or a $(CH_2CH_2O)_qH$ group, m, n and p together stand for 0 or numbers of 1 to 12, q is a number of 1 to 12 and X is halide, alkyl sulfate or alkyl phosphate. Typical examples of esterquats which may be used in accordance with the present invention are products based on caproic acid, caprylic acid, capric acid, lauric acid, myristic acid, palmitic acid, isostearic acid, stearic acid, oleic acid, elaidic acid, arachic acid, behenic acid and erucic acid and the technical mixtures thereof obtained, for example, in the pressure hydrolysis of natural fats and oils. Technical $C_{12/18}$ cocofatty acids and, in particular, partly hydrogenated $C_{16/18}$ tallow or palm oil fatty acids and $C_{16/18}$ fatty acid cuts rich in elaidic acid are preferably used. To produce the quaternized esters, the fatty acids and the triethanolamine may be used in a molar ratio of 1.1:1 to 3:1. With the performance properties of the esterquats in mind, a ratio of 1.2:1 to 2.2:1 and preferably 1.5:1 to 1.9:1 has proved to be particularly advantageous. The preferred esterquats are technical mixtures of mono-, di- and triesters with an average degree of esterification of 1.5 to 1.9 and are derived from technical $C_{16/18}$ tallow or palm oil fatty acid (iodine value 0 to 40). In performance terms, quaternized fatty acid triethanolamine ester salts corresponding to formula (III), in which $R^6CO$ is an acyl group containing 16 to 18 carbon atoms, $R^7$ has the same meaning as $R^6CO$, $R^8$ is hydrogen, $R^9$ is a methyl group, m, n and p stand for 0 and X stands for methyl sulfate, have proved to be particularly advantageous.

Besides the quaternized fatty acid triethanolamine ester salts, other suitable esterquats are quaternized ester salts of fatty acids with diethanolalkyamines corresponding to formula (IV):

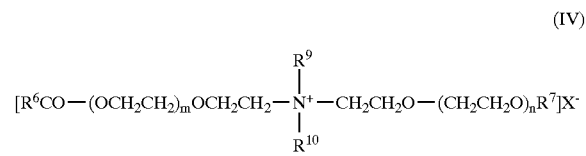

in which $R^6CO$ is an acyl group containing 6 to 22 carbon atoms, $R^7$ is hydrogen or has the same meaning as $R^6CO$, $R^9$ and $R^{10}$ independently of one another are alkyl groups containing 1 to 4 carbon atoms, m and n together stand for 0 or numbers of 1 to 12 and X stands for halide, alkyl sulfate or alkyl phosphate.

Finally, another group of suitable esterquats are the quaternized ester salts of fatty acids with 1,2-dihydroxypropyl dialkylamines corresponding to formula (V):

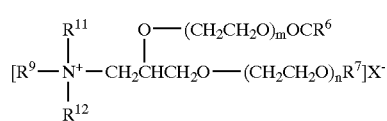

in which $R^6CO$ is an acyl group containing 6 to 22 carbon atoms, $R^7$ is hydrogen or has the same meaning as $R^6CO$, $R^9$, $R^{11}$ and $R^{12}$ independently of one another are alkyl groups containing 1 to 4 carbon atoms, m and n together stand for 0 or numbers of 1 to 12 and X stands for halide, alkyl sulfate or alkyl phosphate.

Finally, other suitable esterquats are substances in which the ester bond is replaced by an amide bond and which—preferably based on diethylenetriamine—correspond to formula (VI):

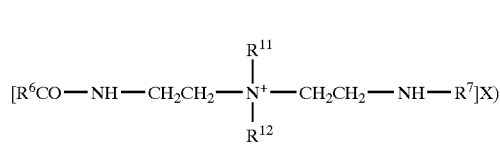

in which $R^6CO$ is an acyl group containing 6 to 22 carbon atoms, $R^7$ is hydrogen or has the same meaning as $R^6CO$, $R^{11}$ and $R^{12}$ independently of one another are alkyl groups containing 1 to 4 carbon atoms and X is halide, alkyl sulfate or alkyl phosphate. Amide esterquats such as these are commercially obtainable, for example, under the name of Incroquat (Croda).

So far as the choice of the preferred fatty acids and the optimal degree of esterification are concerned, the examples mentioned for (III) also apply to the esterquats corresponding to formulae (IV) and (VI). The esterquats are normally marketed in the form of 50 to 90% by weight solutions in alcohol which may readily be diluted as required with water. The esterquats may be used in quantities of 0.1 to 10% by weight and are preferably used in quantities of 1 to 3% by weight and more particularly in quantities of 1 to 3% by weight, based on the keratin-reducing substance or the oxidizing agent.

Protein Hydrolyzates

Protein hydrolyzates are degradation products of animal or vegetable proteins, for example collagen, elastin or keratin, preferably almond and potato protein and more particularly wheat, rice and soya protein, which are obtained by acidic, alkaline and/or enzymatic hydrolysis and thereafter have an average molecular weight of 600 to 4,000 and preferably 2,000 to 3,500. Although protein hydrolyzates are not surfactants in the accepted sense because they lack a hydrophobic residue, they are often used for formulating surface-active compositions by virtue of their dispersing properties. Overviews of the production and use of protein hydrolyzates have been published, for example, by G. Schuster and A. Domsch in Seifen, Öle, Fette, Wachse, 108, 177 (1982) and Cosm. Toil. 99, 63 (1984), by H. W. Steisslinger in Parf. Kosm. 72, 556 (1991) and by F. Aurich et al. in Tens. Surf. Det. 29, 389 (1992). Vegetable protein hydrolyzates based on wheat gluten or rice protein, of which the production is described in German patents DE 19502167 C1 and DE 19502168 C1 (Henkel), are preferably used. The protein hydrolyzates may also be cationically or anionically modified for the purposes of the process according to the invention.

Cationic derivatives are obtained by reaction with compounds which normally contain quaternary ammonium groups or by reaction with corresponding amines and subsequent quaternization. A number of such quaternary protein hydrolyzates are commercially obtainable, including for example:

cationic collagen hydrolyzate, for example the product marketed as Lamequat® L (INCI name: Lauryldimonium Hydroxypropyl Hydrolyzed Collagen; Chemische Fabrik Grünau), cationic keratin hydrolyzate, for example the product marketed as Croquat® (INCI name: Cocodimonium Hydroxypropyl Hydrolyzed Keratin; Croda)

cationic wheat hydrolyzate obtainable as Gluadin® WQ (CTFA name: Lauryldimonium Hydroxypropyl Hydrolyzed Wheat Protein; Henkel KGaA)

the product obtainable as Crotein® Q (INCI name: Steartrimonium Hydrolyzed Animal Protein (Croda) and the quaternized protein hydrolyzate obtainable as Lexein® QX 3000 (Inolex).

Anionic derivatives of protein hydrolyzates are normally obtained by reaction of the protein hydrolyzates with organic acids. Such acids are, for example, oleic acid, myristic acid, undecylenic acid, cocofatty acid and abietic acid. The condensates may also be present in the form of salts, more particularly sodium, potassium and triethanolamine salts. The condensates based on collagen hydrolyzate also bear the INCI names Oleoyl Hydrolyzed Animal Protein, Myristoyl Hydrolyzed Animal Protein, Oleoyl Hydrolyzed Animal Collagen, Potassium Coco Hydrolyzed Animal Protein, TEA Abietoyl Hydrolyzed Animal Collagen, Potassium Undecylenoyl Hydrolyzed Animal Collagen and TEA Coco Hydrolyzed Animal Collagen. Commercial products are, for example, Lamepon® LPO, Lamepon® 4 SK, Lamepon® UD, Lamepon® 460, Lamepon® PA TR, Lamepon® ST 40 and Lamepon® S (Grünau) and Lexein® A 240, Lexein® S 620 and Lexein® A 520 (Inolex). Condensation products of elastin hydrolyzates with fatty acids, for example lauric acid (INCI name: Lauroyl Hydrolyzed Animal Elastin) may also be used. Crolastin® AS (Croda) is a corresponding commercial product. A Sodium Cocoyl Hydrolyzed Wheat Protein is commercially obtainable as Gluadin® WK (Henkel KGaA). Other commercial products suitable for use in accordance with the invention are Lexein® A 200 (Inolex), Lamepon® PO-TR, Lamepon® PA-K, Lamepon® S-MV and Lamepon® S-TR (Grünau) and Crotein® CCT (Croda).

The optionally cationically or anionically modified protein hydrolyzates may be used in the process according to the invention in quantities of 0.1 to 10, preferably 0.5 to 5 and more particularly 1 to 3% by weight, based on the keratin-reducing substance or the oxidizing agent.

Commercial Applications

The use of esterquats results in wave lotions and fixing solutions which not only are mild and show excellent hair-shaping properties, they also do not thicken, even when stored at elevated temperature, and have an advantageous Brookfield viscosity of 4,000 to 7,000 mPas. The present invention also relates to the use of water-based preparations of the keratin-reducing substance and/or the oxidizing agent containing (a) alkoxylated carboxylic acid esters and (b) fatty acid partial glycerides for the production of wave lotions and fixing solutions in which they may each be present in quantities of 0.1 to 20, preferably 0.5 to 10 and more particularly 1 to 5% by weight, with the proviso that the quantities shown add up to 100% by weight.

The following terms are used hereinafter:
"wave lotion" for the aqueous preparation of the keratin-reducing substance,
"intermediate rinse" for the first rinse and
"fixing solution" for the aqueous preparation of the oxidizing agent.

The details of the teaching according to the invention are described in the following with reference to permanent wave lotions. However, the corresponding preparations are equally suitable—with the same advantages—for straightening naturally curly or wavy hair.

Wave Lotions

Wave lotions which may be produced using the alkoxylated carboxylic acid esters and fatty acid partial glycerides and which are used in the process according to the invention contain mercaptans known as keratin-reducing substances as a compulsory component. Examples of such compounds are thioglycolic acid, thiolactic acid, dithiodiglycolic acid, glyceryl monothioglycolate (pH 6–8), thiomalic acid, mercaptoethane sulfonic acid and salts and esters thereof, cysteamine, cysteine, Bunte salts and alkali metal salts of sulfurous acid. The alkali metal or ammonium salts of thioglycolic acid and/or thiolactic acid and the free acids are particularly suitable. They are used in the wave lotions in concentrations of preferably 0.5 to 1.0 mol/kg at a pH value of 5 to 12, preferably 7 to 9.5 and more particularly 6.0 to 8.0. The wave lotions may be formulated as ready-to-use mixtures which may be directly applied either by the hairdresser or by the end user. However, it has proved to be advantageous or necessary in some cases to formulate the lotions as so-called two-component mixtures which are mixed by the user to give the ready-to-use wave lotion. In this case, one formulation contains the reducing agent in a suitable carrier, for example water or an emulsion.

Fixing Solutions

A compulsory ingredient of the fixing preparation which may be produced using the alkoxylated carboxylic acid esters and fatty acid partial glycerides and which are also used in the process according to the invention are oxidizing agents, for example sodium bromate, potassium bromate, hydrogen peroxide, and the stabilizers normally used to stabilize aqueous hydrogen peroxide preparations. The pH value of such aqueous hydrogen peroxide preparations, which normally contain about 0.5 to 3.5% by weight $H_2O_2$, is preferably in the range from 2 to 4. It is adjusted by inorganic acids, preferably phosphoric acid. Bromate-based fixing preparations contain the bromates in concentrations of normally 1 to 10% by weight, the pH value of the solutions being adjusted to pH 4–8. Enzyme-based (for example peroxidase-based) fixing preparations containing only small quantities, if any, of oxidizing agents, more especially $H_2O_2$, are also suitable. The oxidizing agent may preferably be formulated as a two-component system. The two components, of which one is preferably a hydrogen peroxide solution or an aqueous solution of another oxidizing agent while the other contains the other constituents, are also mixed just before use.

Surfactants

Both the wave lotions and the fixing solutions may contain other surfactants in small quantities. In the context of the invention, small quantities are quantities of less than 70% and more particularly less than 50% active substance. In principle, other surfactants are any of the surfactants known for hair treatment preparations, more particularly in the hair shaping field. Such surfactants are:

Anionic surfactants such as, for example, soaps, alkyl benzene-sulfonates, alkanesulfonates, olefin sulfonates, alkylether sulfonates, glycerol ether sulfonates, α-methyl ester sulfonates, sulfofatty acids, alkyl sulfates, fatty alcohol ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids such as, for example, acyl lactylates, acyl tartrates, acyl glutamates and acyl aspartates, alkyl oligoglucoside sulfates, protein fatty acid condensates (particularly wheat-based vegetable products) and alkyl (ether) phosphates. If the anionic surfactants contain polyglycol ether chains, they may have a conventional homolog distribution although they preferably have a narrow-range homolog distribution. Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, optionally partly oxidized alk(en)yl oligoglycosides or glucuronic acid derivatives, fatty acid-N-alkyl glucamides, protein hydrolyzates (more particularly wheat-based vegetable products), polyol fatty acid esters, sugar esters, sorbitan esters, polysorbates and amine oxides. If the nonionic surfactants contain polyglycol ether chains, the polyglycol ether chains may have a conventional homolog distribution, although they preferably have a narrow homolog distribution. Typical examples of cationic surfactants are quaternary ammonium compounds, such as dimethyl distearyl ammonium chloride for example, and esterquats, more particularly quaternized fatty acid trialkanolamine ester salts. Typical examples of amphoteric or zwitterionic surfactants are alkylbetaines, alkylamidobetaines, amino-propionates, aminoglycinates, imidazolinium betaines and sulfobetaines. The surfactants mentioned are all known compounds. Information on their structure and production can be found in relevant synoptic works, cf. for example J. Falbe (ed.), "Surfactants in Consumer Products", Springer Verlag, Berlin, 1987, pages 54 to 124 or J. Falbe (ed.), "Katalysatoren, Tenside und Mineralöladditive (Catalysts, Surfactants and Mineral Oil Additives)", Thieme Verlag, Stuttgart, 1978, pages 123–217. The expert will preferably select those surfactants which are advantageous by virtue of their low irritation potential or their swelling effect. In one particularly advantageous embodiment of the invention, however, neither the wave lotions nor the fixing solutions contain other surfactants than alkyl polyglycosides, fatty acid-N-alkyl glucamides, esterquats and vegetable protein hydrolyzates. The intermediate rinse also preferably contains no other components than water and dissolved salts. In another advantageous embodiment, the wave lotions and fixing solutions have the same surfactant base.

Auxiliaries and Additives

Besides the preferred auxiliaries and additives, such as esterquats or other surfactants, protein hydrolyzates, wave lotions and fixing solutions, the wave lotions may additionally contain any of the ingredients known for this purpose such as, for example, pearlizing waxes, consistency factors, thickeners, polymers, silicone compounds, fats, waxes, stabilizers, biogenic film formers, swelling agents, hydrotropes, structurants, complexing agents, opacifiers, propellents, preservatives, solubilizers, perfume oils, dyes and the like.

Suitable pearlizing waxes are, for example, alkylene glycol esters, especially ethylene glycol distearate; fatty acid alkanolamides, especially cocofatty acid diethanolamide; partial glycerides, especially stearic acid monoglyceride; esters of polybasic, optionally hydroxysubstituted carboxylic acids with fatty alcohols containing 6 to 22 carbon atoms, especially long-chain esters of tartaric acid; fatty compounds, such as for example fatty alcohols, fatty ketones, fatty aldehydes, fatty ethers and fatty carbonates which contain in all at least 24 carbon atoms, especially laurone and distearylether; fatty acids, such as stearic acid, hydroxystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups and mixtures thereof.

The consistency factors mainly used are fatty alcohols or hydroxyfatty alcohols containing 12 to 22 and preferably 16 to 18 carbon atoms and also partial glycerides, fatty acids or hydroxyfatty acids. A combination of these substances with alkyl oligoglucosides and/or fatty acid N-methyl glucamides of the same chain length and/or polyglycerol poly-12-hydroxystearates is preferably used.

Suitable thickeners are, for example, Aerosil types (hydrophilic silicas), polysaccharides, more especially xanthan gum, guar guar, agar agar, alginates and tyloses, carboxymethyl cellulose and hydroxyethyl cellulose, also relatively high molecular weight polyethylene glycol monoesters and diesters of fatty acids, polyacrylates (for example Carbopols® [Goodrich] or Synthalens® [Sigma]), polyacrylamides, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethoxylates or alkyl oligoglucosides and electrolytes, such as sodium chloride and ammonium chloride.

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat® L, Grünau), quaternized wheat polypeptides, polyethyleneimine, cationic silicone polymers such as, for example, amodimethicone, copolymers of adipic acid and dimethylamino-hydroxypropyl diethylenetriamine (Cartaretine®, Sandoz), copolymers of acrylic acid with dimethyl diallyl ammonium chloride (Merquat®) 550, Chemviron), polyaminopolyamides as described, for example, in FR 2252840 A and crosslinked water-soluble polymers thereof, cationic chitin derivatives such as, for example, quaternized chitosan, optionally in microcrystalline distribution, condensation products of dihaloalkyls, for example dibromobutane, with bis-dialkylamines, for example bis-dimethylamino-1,3-propane, cationic guar gum such as, for example, Jaguar®CBS, Jaguar®C-17, Jaguar®C-16 of Celanese, quaternized ammonium salt polymers such as, for example, Mirapol® A-15, Mirapol® AD-1, Mirapol® AZ-1 of Miranol.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/acrylate copolymers, octylacrylamide/methyl methacrylate/tert.-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones.

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. Other suitable silicone compounds are simethicones which are mixtures of dimethicones with an average chain length of 200 to 300 dimethylsiloxane units and hydrogenated silicates. A detailed overview of suitable volatile silicones can be found in Todd et al. in Cosm. Toil. 91, 27 (1976).

Typical examples of fats are glycerides while suitable waxes are inter alia natural waxes such as, for example, candelilla wax, carnauba wax, Japan wax, espartograss wax, cork wax, guaruma wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes, microwaxes; chemically modified waxes (hard waxes) such as, for example, montan ester waxes, sasol waxes, hydrogenated jojoba waxes and synthetic waxes such as, for example, polyalkylene waxes and polyethylene glycol waxes.

Metal salts of fatty acids such as, for example, magnesium, aluminium and/or zinc stearate or ricinoleate may be used as stabilizers.

In addition, hydrotropes, for example ethanol, isopropyl alcohol or polyols, may be used to improve flow behavior. Suitable polyols preferably contain 2 to 15 carbon atoms and at least two hydroxyl groups. The polyols may contain other functional groups, more especially amino groups, or may be modified with nitrogen. Typical examples are glycerol;

alkylene glycols such as, for example, ethylene glycol, diethylene glycol, propylene glycol, butylene glycol, hexylene glycol and polyethylene glycols with an average molecular weight of 100 to 1000 dalton;

technical oligoglycerol mixtures with a degree of self-condensation of 1.5 to 10 such as, for example, technical diglycerol mixtures with a diglycerol content of 40 to 50% by weight;

methylol compounds such as, in particular, trimethylol ethane, trimethylol propane, trimethylol butane, pentaerythritol and dipentaerythritol;

lower alkyl glucosides, particularly those containing 1 to 8 carbon atoms in the alkyl group, for example methyl and butyl glucoside;

sugar alcohols containing 5 to 12 carbon atoms, for example sorbitol or mannitol, sugars containing 5 to 12 carbon atoms, for example glucose or sucrose;

amino sugars, for example glucamine;

dialcoholamines, such as diethanolamine or 2-aminopropane-1,3-diol.

Suitable preservatives are, for example, phenoxyethanol, formaldehyde solution, parabens, pentanediol or sorbic acid and the other classes of compounds listed in Appendix 6, Parts A and B of the Kosmetikverordnung ("Cosmetics Directive"). Suitable structurants are, for example, glucose or maleic acid. EDTA, phenazetin, NTA and phosphonic acids may be used as complexing agents. A suitable opacifier is, for example, latex.

Suitable perfume oils are mixtures of natural and synthetic perfumes. Natural perfumes include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamon, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones, α-isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable perfume. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, ladanum oil and lavendin oil. The following are preferably used either individually or in the form of mixtures: bergamot oil, dihydromyrcenol, lilial, lyral, citronellol, phenylethyl alcohol, α-hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, β-damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Suitable dyes are any of the substances suitable and approved for cosmetic purposes as listed, for example, in the publication "Kosmetische Färbemittel" of the Farbstoffkommission der Deutschen Forschungs-gemeinschaft, Verlag Chemie, Weinheim, 1984, pages 81 to 106, These dyes are normally used in concentrations of 0.001 to 0.1% by weight, based on the mixture as a whole.

The total percentage content of auxiliaries and additives may be from 1 to 50% by weight and is preferably from 5 to 40% by weight, based on the particular preparation. The preparations may be produced by standard cold or hot processes and are preferably produced by the phase inversion temperature method.

Both the wave lotions and the fixing solutions may be formulated as creams, gels or liquids. They may also be made up as foam aerosols which are packed in aerosol cans with a foam valve together with a liquefied gas such as, for example, propane/butane mixtures, nitrogen, carbon dioxide, air, dinitrogen oxide, dimethyl ether, chlorofluorocarbon propellants or mixtures thereof. The wave lotions and fixing solutions may be combined with any typical pretreatments, intermediate rinses and/or aftertreatments (to improve conditioning and style retention).

EXAMPLES

The following Examples illustrate the preparation of fixing solutions based on the surfactants according to the invention (1, 2, 3) and panthenol (C1, C2). To produce the preparations, water is heated to 75° C., the alkoxylated carboxylic acid esters and partial glycerides and the other surfactants, if any, are stirred in and homogenized. The mixture is then left to cool to 40° C. and the other ingredients are stirred in. In addition, human hair (Alkinco 6634) is subjected to thermal analysis after application of the mixtures set out in Table 1. The transition point of the treated hair sample as compared with an untreated hair sample is measured by dynamic differential calorimetry (HP-DSC; F. J. Wortmann et al., J. Appi. Polym. Sci. 1993, 48, pp. 137 et seq.; untreated hair sample 152.5° C.). The composition of the fixing solutions is shown in Table 1.

TABLE 1

| Fixing solutions (quantities = % by weight) | | | | |
|---|---|---|---|---|
| Composition/performance | 1 | 2 | 3 | C1 |
| $C_{12/18}$ coconut fatty acid + 2EO methyl ester | 5 | 3 | 10 | — |
| Monomuls ® 90-O18 Glyceryl Oleate | 10 | 3 | 5 | — |
| Dehyquart ® C 4046 Cetearyl Alcohol (and) Dipalmitoylethyl Hydroxyethylmonium Methosulfate (and) Cetearyl Sulfate | — | 1.0 | — | — |
| Panthenol | — | — | — | 3.0 |
| Gluadin ® WQ Laurdimonium Hydroxypropyl Hydrolyzed Wheat Protein | — | — | 1.2 | 1.2 |
| Turpinal ® SL Editronic Acid | 0.3 | 0.3 | 0.3 | 0.3 |
| Hydrogen peroxide (35% by weight) | 7.5 | 7.5 | 7.5 | 7.5 |
| Water | | to 100 | | |
| pH value | 2.5 | 2.7 | 2.8 | 2.8 |
| Brookfield viscosity [mPas] (23° C., Sp. TC, 10 r.p.m.) | 4900 | 3600 | 6150 | 6150 |
| Transition point (HP-DSC) | 140.4 | 150.7 | 151.1 | 149.8 |

What is claimed is:

1. A process for deforming keratin fibers comprising:
   (a) mechanically deforming the keratin fibers to form mechanically deformed keratin fibers; and
   (b) contacting the keratin fibers prior to and/or after the keratin fibers are mechanically deformed, with an aqueous composition containing:
      (i) from about 0.1 to 20% by weight of an alkoxylated carboxylic acid ester; and
      (ii) from about 0.1 to about 20% by weight of a fatty acid partial glyceride, all weights being based on the weight of the composition.

2. The process of claim 1 wherein the alkoxylated carboxylic acid ester corresponds to formula I:

$$R^1CO(OAlk)_nOR^2 \qquad (I)$$

wherein $R^1CO$ is a linear or branched, saturated or unsaturated acyl group having from about 10 to 18 carbon atoms, AlkO is a $CH_2CH_2O$ group, n is a number from about 5 to 20, and $R^2$ is a methyl group.

3. The process of claim 1 wherein the alkoxylated carboxylic acid ester is present in the composition in an amount of from about 0.5 to 10% by weight, based on the weight of the composition.

4. The process of claim 1 wherein the alkoxylated carboxylic acid ester is present in the composition in an amount of from about 1 to 5% by weight, based on the weight of the composition.

5. The process of claim 1 wherein the fatty acid partial glyceride is present in the composition in an amount of from about 0.5 to 10% by weight, based on the weight of the composition.

6. The process of claim 1 wherein the fatty acid partial glyceride is present in the composition in an amount of from about 1 to 5% by weight, based on the weight of the composition.

7. The process of claim 1 wherein the aqueous composition further contains an esterquat.

8. The process of claim 7 wherein the esterquat is present in the composition in an amount of from about 0.1 to 10% by weight, based on the weight of the composition.

9. The process of claim 1 wherein the aqueous composition has a Brookfield viscosity of from about 4,000 to 7,000 mPas.

10. The process of claim 1 wherein the aqueous composition further contains a modified protein hydrolyzate selected from the group consisting of a cationically modified protein hydrolyzate, an anionically modified protein hydrolyzate, and mixtures thereof.

11. The process of claim 10 wherein the modified protein hydrolyzate is present in the composition in an amount of from about 0.1 to 10% by weight, based on the weight of the composition.

* * * * *